(12) United States Patent
Ingram et al.

(10) Patent No.: US 11,690,939 B2
(45) Date of Patent: Jul. 4, 2023

(54) SYSTEM FOR ASEPTIC COLLECTION AND ENTERAL DELIVERY

(71) Applicant: Avent, Inc., Alpharetta, GA (US)

(72) Inventors: Aaron N. Ingram, Canton, GA (US); Anthony C. Lair, Alpharetta, GA (US); Mark Martin Costello, County Mayo (IE); Tony Doherty, County Mayo (IE)

(73) Assignee: Avent, Inc., Alpharetta, GA (US)

( * ) Notice: Subject to any disclaimer, the term of this patent is extended or adjusted under 35 U.S.C. 154(b) by 453 days.

(21) Appl. No.: 16/869,662

(22) Filed: May 8, 2020

(65) Prior Publication Data

US 2020/0261632 A1 Aug. 20, 2020

Related U.S. Application Data

(60) Division of application No. 15/232,460, filed on Aug. 9, 2016, now Pat. No. 10,682,447, which is a
(Continued)

(51) Int. Cl.
*A61M 1/06* (2006.01)
*A61J 15/00* (2006.01)
*A61J 9/08* (2006.01)

(52) U.S. Cl.
CPC .............. *A61M 1/062* (2014.02); *A61J 15/00* (2013.01); *A61J 15/0076* (2015.05); *A61M 1/06* (2013.01); *A61J 9/085* (2013.01); *A61J 2200/76* (2013.01)

(58) Field of Classification Search
CPC .............. A61M 5/158; A61M 5/14216; A61M 5/14212; A61M 1/062; A61M 1/06; A61M 15/00; A61M 5/1456; A61M 5/14566; A61J 15/0076; A61J 9/085; A61J 15/00; A61J 2200/76
See application file for complete search history.

(56) References Cited

U.S. PATENT DOCUMENTS 2,303,997 A   12/1942   Hogg
2,628,906 A   2/1953    Horan
(Continued)

FOREIGN PATENT DOCUMENTS

EP    0 481 250 A1       4/1992
WO    WO 2009/141510 A1  11/2009

OTHER PUBLICATIONS

International Search Report & Written Opinion for PCT/US2011/045481; dated Jan. 4, 2012; 19 pgs.

*Primary Examiner* — Theodore J Stigell
(74) *Attorney, Agent, or Firm* — Dority & Manning, P.A.

(57) ABSTRACT

A container for collecting, storing and dispensing fluid, as in enteral feeding and/or medication deliver to neonatal infants. The container includes a hollow tube with a body, a first end, a second end, and an outer diameter. The hollow tube is configured to receive a movable plunger that advances and retracts therein to define a variable contained volume. The container also includes a sealing head assembly removably mounted at an end of the hollow tube. The sealing head assembly has a diameter or outside dimension that is substantially similar or identical to a corresponding outside diameter or dimension of the hollow tube, so that the container lies flat within the receiver of an enteral feeding pump.

5 Claims, 9 Drawing Sheets

Related U.S. Application Data continuation of application No. 13/561,309, filed on Jul. 30, 2012, now Pat. No. 9,433,562, which is a continuation-in-part of application No. 13/191,721, filed on Jul. 27, 2011, now Pat. No. 9,586,734.

(60) Provisional application No. 61/513,004, filed on Jul. 29, 2011, provisional application No. 61/418,961, filed on Dec. 2, 2010, provisional application No. 61/388,057, filed on Sep. 30, 2010, provisional application No. 61/368,023, filed on Jul. 27, 2010.

(56) References Cited

U.S. PATENT DOCUMENTS

| | | | |
|---|---|---|---|
| 3,093,256 A | 6/1963 | Woodbury, Jr. | |
| 3,113,873 A | 12/1963 | Krause | |
| 3,804,952 A | 4/1974 | MacDonald | |
| 3,946,888 A | 3/1976 | Tonkin | |
| 3,977,405 A | 8/1976 | Yanase | |
| 4,010,861 A | 3/1977 | Welten | |
| D251,612 S | 4/1979 | Lagergren et al. | |
| 4,313,439 A * | 2/1982 | Babb | A61M 5/1454 604/246 |
| 4,323,067 A * | 4/1982 | Adams | A61M 1/06 604/74 |
| 4,339,046 A | 7/1982 | Coen | |
| 4,392,851 A | 7/1983 | Elias | |
| 4,493,348 A | 1/1985 | Lemmons | |
| 4,673,396 A | 6/1987 | Urbaniak | |
| 4,685,577 A | 8/1987 | Chen | |
| 4,749,109 A | 6/1988 | Kamen | |
| 4,857,051 A | 8/1989 | Larsson | |
| 4,869,381 A | 9/1989 | Agner | |
| 4,898,291 A | 2/1990 | Sailors | |
| 5,035,340 A | 7/1991 | Timmons | |
| 5,356,016 A | 10/1994 | Wiedemann | |
| 5,366,115 A | 11/1994 | Kersten et al. | |
| 5,423,791 A | 6/1995 | Bartlett | |
| 5,524,783 A | 6/1996 | Popoff | |
| 5,554,116 A | 9/1996 | Fu-Hsiang | |
| 5,653,353 A | 8/1997 | Otto et al. | |
| 5,787,898 A | 8/1998 | Freimann | |
| 5,799,808 A | 9/1998 | Oh | |
| 5,878,899 A | 3/1999 | Manganiello et al. | |
| D408,922 S | 4/1999 | Garcia | |
| 5,988,448 A | 11/1999 | Foth | |
| 6,050,431 A | 4/2000 | Koehnke | |
| 6,050,434 A | 4/2000 | McNab | |
| 6,138,848 A | 10/2000 | Fermo | |
| 6,305,563 B1 | 10/2001 | Elliott | |
| 6,415,937 B1 | 7/2002 | DeJong et al. | |
| 6,422,415 B1 | 7/2002 | Manganiello | |
| 6,465,024 B1 | 10/2002 | Di Scala et al. | |
| 6,485,465 B2 | 11/2002 | Moberg et al. | |
| 6,666,852 B2 | 12/2003 | Niedospial, Jr. | |
| 6,732,872 B1 | 5/2004 | Gregro et al. | |
| 6,832,994 B2 | 12/2004 | Niedospial, Jr. et al. | |
| 6,871,751 B2 | 3/2005 | Kerns et al. | |
| 7,032,764 B2 | 4/2006 | Viggiano | |
| 7,063,684 B2 | 6/2006 | Moberg | |
| 7,472,797 B2 | 1/2009 | Ostrowski | |
| 7,658,294 B2 | 2/2010 | Housley et al. | |
| 7,841,581 B2 | 11/2010 | Thorne, Jr. et al. | |
| 7,849,559 B2 | 12/2010 | Lindmark et al. | |
| 8,162,916 B2 | 4/2012 | Knight | |
| 8,231,597 B2 | 7/2012 | Knight | |
| 8,262,616 B2 * | 9/2012 | Grant | A61M 5/1456 604/151 |
| 8,366,697 B2 | 2/2013 | Knight | |
| 8,979,818 B2 | 3/2015 | Sherman et al. | |
| 8,998,879 B2 | 4/2015 | Sherman et al. | |
| 9,283,148 B2 * | 3/2016 | Hyun | A61M 5/178 |
| 9,433,562 B2 | 9/2016 | Ingram et al. | |
| 2002/0088827 A1 | 7/2002 | Colucci | |
| 2005/0101908 A1 | 5/2005 | Atkin et al. | |
| 2010/0175777 A1 | 7/2010 | Laskowski | |
| 2011/0054436 A1 | 3/2011 | Griffis, III et al. | |
| 2012/0265169 A1 | 10/2012 | Sherman et al. | |
| 2014/0135683 A1 | 5/2014 | Hradisky et al. | |
| 2015/0065996 A1 | 3/2015 | Bartlett, II et al. | |
| 2015/0133894 A1 | 5/2015 | Sherman et al. | |
| 2015/0148783 A1 | 5/2015 | Bartlett, II et al. | |
| 2015/0196696 A1 | 7/2015 | Sherman et al. | |

* cited by examiner

SYSTEM FOR ASEPTIC COLLECTION AND ENTERAL DELIVERY

CROSS-REFERENCE TO RELATED APPLICATIONS

The present application is a divisional of U.S. application Ser. No. 15/232,460, filed on Aug. 9, 2016, which is a continuation of U.S. Non-Provisional patent application Ser. No. 13/561,309 filed Sep. 6, 2016 (issued as U.S. Pat. No. 9,433,562), which claims priority benefit to U.S. Provisional Patent Application Ser. No. 61/513,004 filed Jul. 29, 2011, and which is a continuation-in-part of U.S. Non-Provisional patent application Ser. No. 13/191,721 filed Mar. 7, 2017 (issued as U.S. Pat. No. 9,586,734), which claims the priority benefit of U.S. Provisional Patent Application Ser. No. 61/368,023 filed Jul. 27, 2010, U.S. Provisional Patent Application Ser. No. 61/388,057 filed Sep. 30, 2010 and U.S. Provisional Patent Application Ser. No. 61/418,961 filed Dec. 2, 2010; all of which are hereby incorporated herein by reference in their entireties.

TECHNICAL FIELD

The present invention relates generally to the field of collection and dispensing of fluids, and more particularly to a collection and dispensing system for biological fluids, such as breast milk and/or dietary or medicinal materials.

BACKGROUND

Maintaining aseptic integrity is of great importance in many fluid collection and dispensing applications. For example, in the delivery of breast milk or formula to premature infants who are unable to feed regularly, freshness and prevention of contamination are critical. The delivery of enteral fluids is often controlled by regulations and medical standards of practice.

In addition to proper collection and dispensing of biological fluids such as breast milk or formula, it is also desirable to provide for the containment, mixing and delivery of pharmaceutical or nutritional supplements. Various consumer and/or professional applications would benefit from improved systems and methods for fluid collection and delivery.

It is to the provision of improved systems and methods for fluid collection and delivery that the present invention is primarily directed.

SUMMARY

In example embodiments, the present invention provides a container for collecting, storing and dispensing fluid. The container includes a hollow tube with an outer circumference diameter. The tube is configured to receive a plunger. The container also includes a circumferential seal assembly secured at one end of the hollow tube. The seal assembly outer diameter is substantially similar to the hollow tube outer diameter.

In one aspect, the invention relates to a container that includes a hollow tube with a body, a first end, a second end, and an outer diameter. In example embodiments, the hollow tube is configured to receive a plunger within the first end. The container also includes a circumferential seal assembly secured at the second end of the hollow tube. The seal assembly includes an external diameter that is substantially similar to the hollow tube outer diameter.

In another aspect, the invention relates to a container that includes a cylindrical tube with a body, a first end, a second end and a threaded region. The container also includes a circumferential seal assembly with a threaded region configured to removably secure to the cylindrical tube threaded region. The circumferential seal assembly includes a diameter that is substantially similar to the hollow tube. The container also includes an annular flange secured to the cylindrical tube first end. The annular flange includes a larger outer diameter than the cylindrical tube and an inner diameter that is substantially similar to the cylindrical tube.

In another aspect, the invention relates to a method of dispensing a fluid. In example forms, the method includes storing a fluid in a container. The container includes a barrel, a plunger that is translationally mounted in the barrel, and a cap for removable attachment to a proximal end of the barrel. The cap includes a resealable port. And the cap and barrel have a substantially continuous outer profile about their external peripheries. The method also includes mounting the container in a dispensing pump and operating the dispensing pump to deliver the fluid through the resealable port.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-13 show example embodiments of fluid collection, containment and dispensing systems according to the invention. In example forms, the fluid collection, containment and dispensing system comprises a primary containment device or container 10 including a hollow, generally cylindrical containment barrel 20, a movable plunger 40, a dispensing and sealing head 60, and a closure cap 90.

The containment barrel 20 comprises a generally tubular body portion or sleeve 22 defining an open interior chamber for containment of a fluid with which the device is to be used, and having circular openings at each end thereof. The interior chamber of the sleeve 22 can have a circumferential internal diameter. The length and inner diameter of the interior chamber may vary depending on the desired application, to provide adequate fluid volume. The containment barrel can have a variety of volumes. Example volumes of the containment barrels can range from about 3 ml to about 100 ml, more preferably about 20 ml to about 60 ml, but can be smaller (FIG. 2B) or larger (FIG. 2A) depending upon the intended application. The containment barrel 20 further comprises a base flange 24 at a first end of the sleeve 22, and a second end opposite the base flange. The base flange 24 optionally has a larger inner diameter opening than the containment barrel 20 diameter for ease of assembly. The base flange 24 can be a single circumferential flat edge projecting radially outward from the first end of the containment barrel 20. (FIGS. 5A, 6A, 8A and 8B). The base flange 24 can alternatively have a pair of opposing coplanar flat edges projecting away from and normal to the first end of the containment barrel 20. The base flange 24 can be fixed around the outer circumference of the containment barrel 20 to have a flush bottom surface with the first end of the sleeve 22. Alternatively, the base flange 24 can be secured to the edge of the first end of the sleeve 22. The base flange 24 can molded with the containment barrel 20 to form a unitary structure. Alternatively, the base flange 24 can be a separately constructed body that is fixed with respect to the containment barrel 20, for example through glue, friction fit, tongue and groove or threading.

Figure 11A:
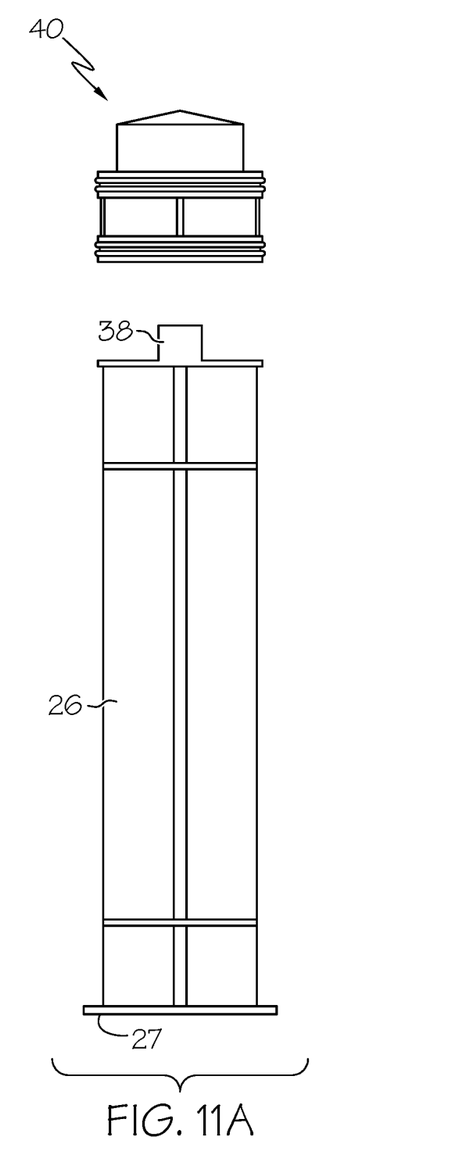
FIGS. 11A & 11B are side views of alternative embodiments of the plunger and plunger body according to example forms of the invention.
Figure 11B:
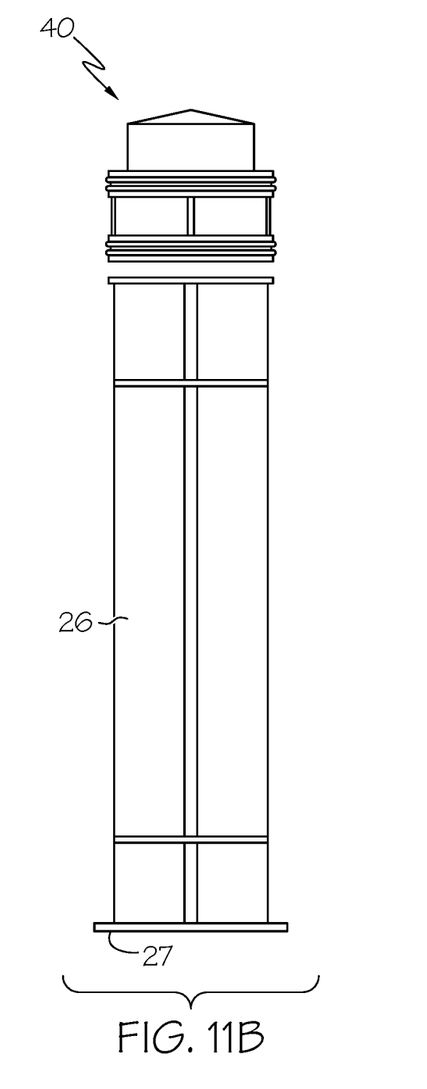

The containment barrel 20 is adapted to receive a plunger comprising a plunger head 40 optionally connected to a plunger handle or body 26, through an opening in the first end of sleeve 22 located at the base flange 24. Alternatively, the plunger head 40 can be designed to enter the syringe sleeve 22 at the end opposite the base flange 24 and the plunger body 26, if provided, connected to the plunger head and extending through the base flange of the syringe sleeve. The plunger head preferably comprises a seal formed of one or more resilient flanges or gaskets, in fluid-tight sealing contact with the inner surface of the containment barrel 22. As shown in greater detail in FIGS. 11A and 11B, an example plunger body 26 includes a pressure plate 27. As shown, the pressure plate is a flat planar plate positioned perpendicularly to the longitudinal axis of the plunger body 26. The pressure plate 27 can be a separate structure secured to the plunger body 26 or alternatively the pressure plate can be molded with the plunger body. The pressure plate 27 has dimensions greater than the cross-sectional dimensions of the plunger body 26, so as shown, the pressure plate extends beyond the outer vertical edges of the plunger body. The example plunger body 26 shown in FIG. 11A has a mounting hub or pin 75 that couples with a corresponding receiver in the plunger head 40, to allow attachment and detachment of the handle body 26 from the sealing head 40. Alternatively as shown in FIG. 11B, the bottom face of the plunger head 40 attaches to the plunger body with a resilient collar, adhesive, or other attachment means.

Figures 1A, 1B, 1C:
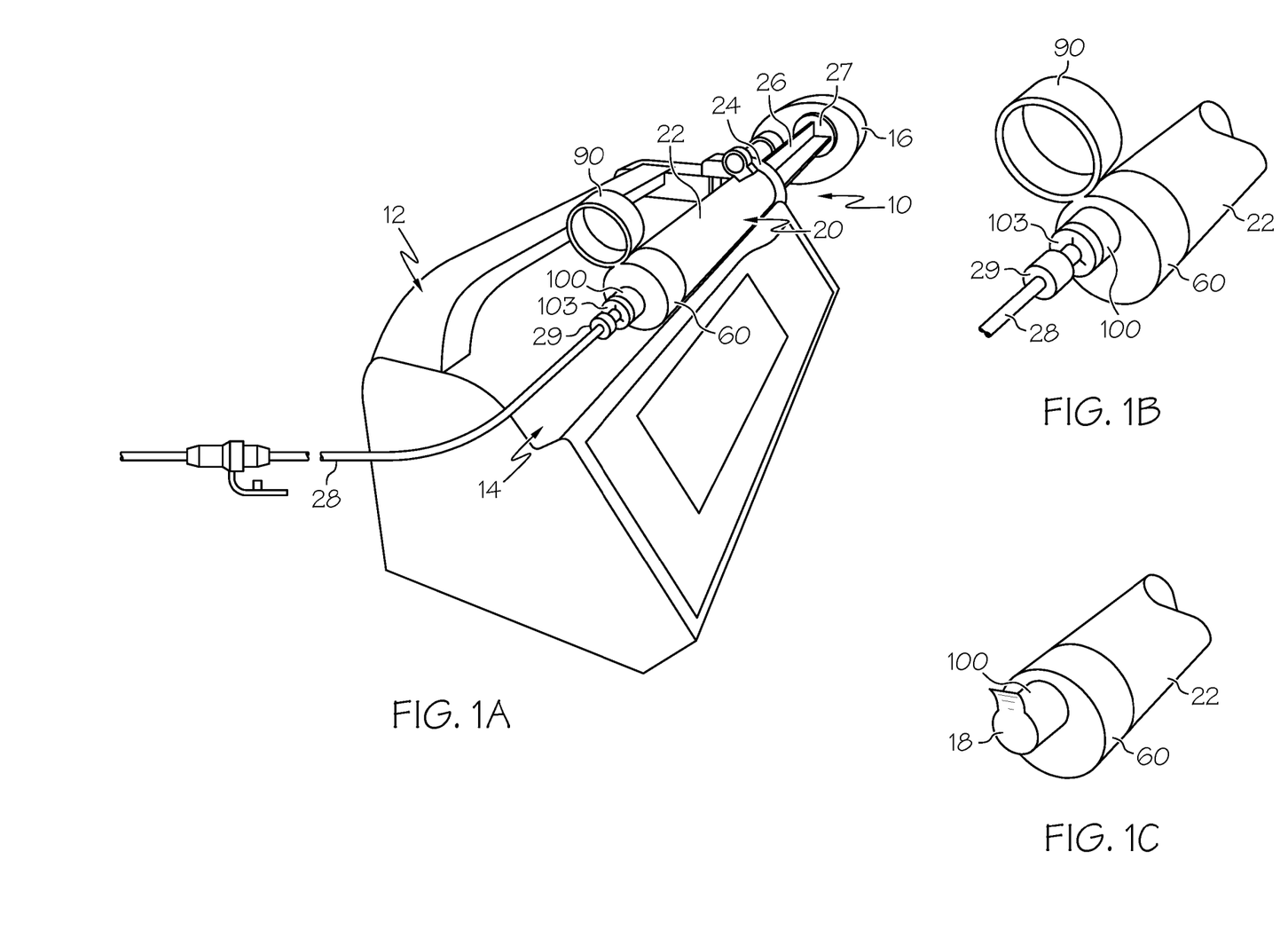
FIG. 1A is a perspective view of the container in use with a pump according to an example embodiment of the present invention.
FIG. 1B is an enlarged perspective view of a first alternative example embodiment of the seal and cap portions of a container.
FIG. 1C is an enlarged perspective view of a second alternative example embodiment of the seal and cap portions of a container.
Figure 2A:
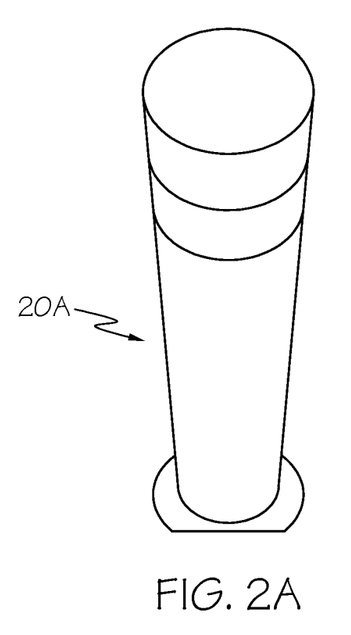
FIGS. 2A and 2B are enlarged perspective views of alternate sizes of containers according to example embodiments of the present invention.
Figure 2B:
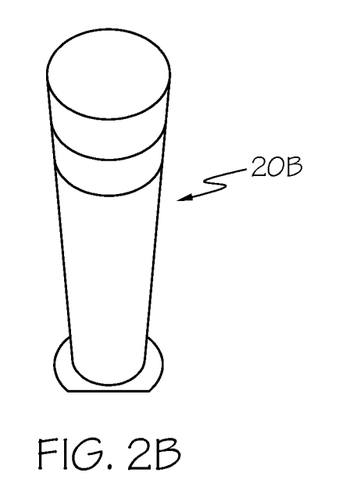
Figure 3A:
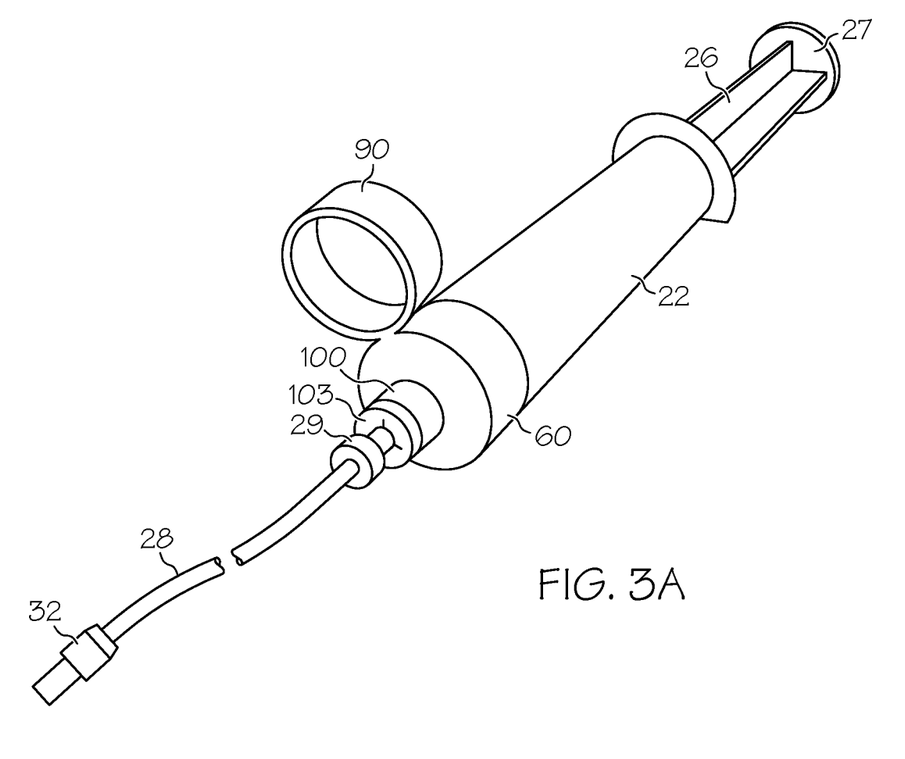
FIG. 3A is an isolated perspective view of the container of FIG. 1A removed from the pump.
Figure 3B:
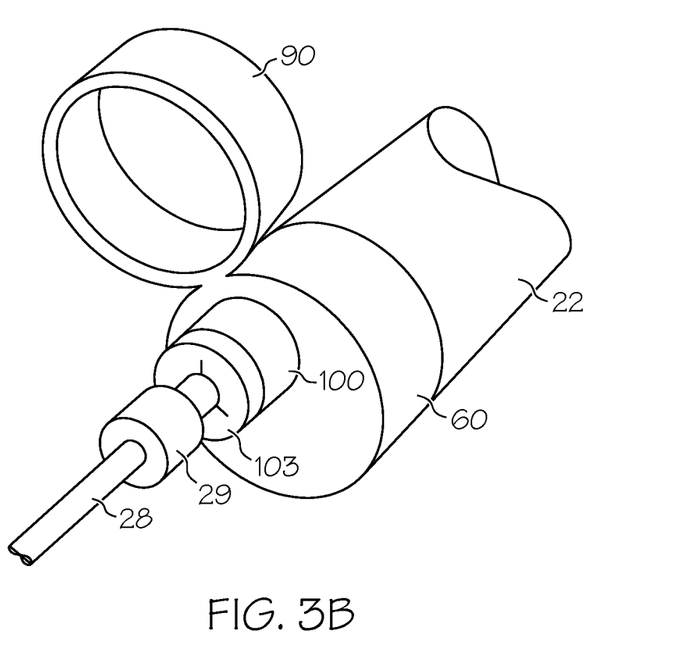
FIG. 3B is an enlarged isolated perspective view of the first alternative example embodiment of the seal and cap of FIG. 1B.
Figure 4:
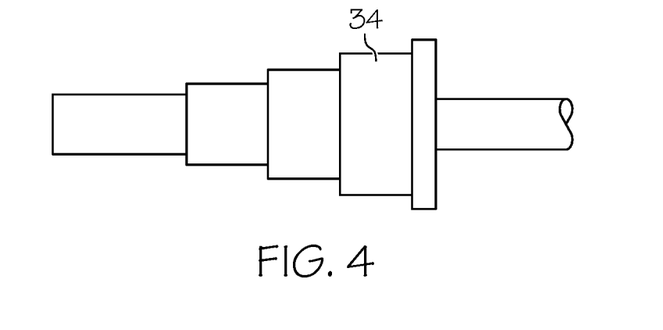
FIG. 4 is a side view of an alternative connector for a container according to an example embodiment.
Figures 5A, 5B:
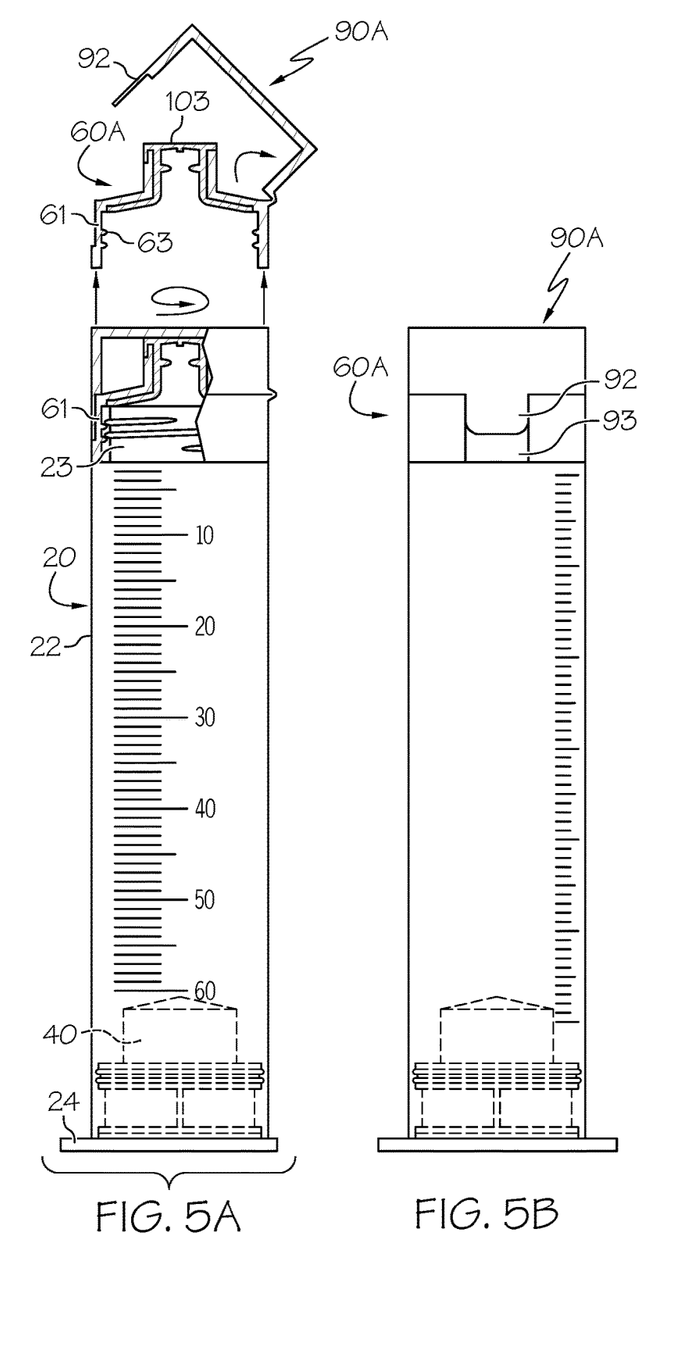
FIG. 5A is a side view in partial cross-section of the first example container shown in FIGS. 1A and 3A, including removed view of the cap and seal arrangement showing the cap in an open state.
FIG. 5B is a side view of the example container shown in FIG. 5A showing the cap in a closed state.
Figure 5C:
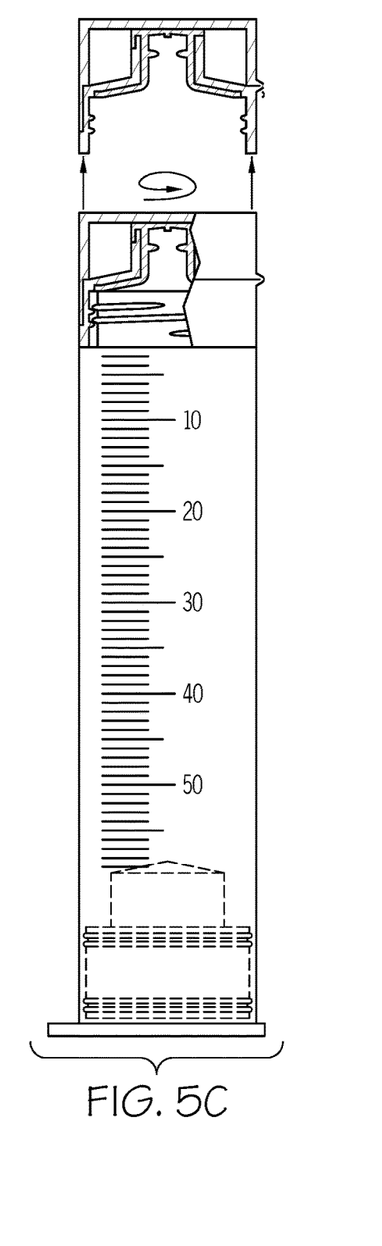
FIG. 5C is a partial cross-sectional side view as shown in FIG. 5A, including a view of the cap removed and in a closed state.

The removable sealing head 60 and containment barrel 20 of the syringe have substantially similar or identical outer diameters and circumferential shapes so as to create a flush and continuous outer surface between them. In this manner, the external dimension and profile of the syringe is substantially smooth and continuous, without any step or discontinuity at the joint between the head 60 and the barrel 20. The sealing head 60 can include a port 100 with a silicon seal 103 to receive a connector 29 of a feeding tube 28 for delivery of fluid to and from the contained volume. As shown, the port 100 can be located at the center of the sealing head 60 (FIGS. 1A & 3A) or in an eccentric or off-center position (FIGS. 1B & 3B). As shown in FIG. 1C and FIGS. 9A-9C, a further example arrangement of the port 100 can be covered with a removable sealing foil 18 instead of, or in addition to, the closure cap 90. A commercially-available feeding tube 28 includes a second connector 32, 34 to introduce fluids from the container 10 into a predetermined recipient. (FIGS. 3A and 4). As shown, the second connector 32, 34 can have variable telescoping stepped diameters to assist with connection. A male-to-male adapter feeding tube 28 as shown for example in FIG. 3A, may be utilized for connection between the female access port 100 of the container and the female fitting of a standard enteral feeding tube. Optionally, the adapter tube 28 has identical male couplings 29, 32 at each end for universal compatibility and reversibility. An alternative coupling configuration is shown in FIG. 4.

As shown in FIG. 1A, the container 10 can be used with a commercially available pump 12, for example a motorized metering pump for enteral feeding of premature infants. A preferred pump 12 includes a semi-cylindrical open channel 14 to receive the barrel 20 of the container 10. The flush and continuous surface diameter between the sleeve 22 and sealing head 60 allows the barrel and sealing head to preferably lay flat within the channel 14. A preferred pump 12 further includes a force application mechanism 16 that applies force onto the pressure plate 27 of the plunger body 26 to move the plunger body through the length of the sleeve 22 at a safe speed. As shown, the container 10 is positioned within the channel 14 so that the base flange 24 is outside of the channel 14 and catches on the side of the pump 12 body in order to be prevented from being forced forward when the force application mechanism 16 applies pressure to the pressure plate 27. The position and design of the flange 24 allows the container 10 to be rotated in order to accommodate a variety of pump designs or configurations. Example commercially available pumps that can be used include the MEDFUSION 3500 and BBRAUN PERFUSER.

As shown in FIG. 5A-FIG. 10, the flush and continuous outer surface contour between the sleeve 22 and sealing head 60 can be achieved through a variety of detachable, semi-permanent or permanent attachment structures. The example shown in FIGS. 5A-5C includes a barrel 22 with a narrowed-diameter male coupling ring 23 having threading on the outer surface. The example sealing head 60A has a circumferential female coupling collar 61 with cooperatively mating threading 63 on the inner surface of its sidewall. The diameter of the circumferential wall 61 is substantially equivalent to the diameter of the barrel 22. And, the outer threading on the ring 23 corresponds with the inner threading on the sealing head 60A for engagement. The sealing head 60A further includes a silicon seal 103 that extends from an external region of the sealing head and along the internal walls. A cap 90A is secured to a location on the sealing head 60A such that the cap can cover the sealing head and flip up or be removed to uncover the sealing head. This cap 90A can be hingedly attached to the sealing head 60A through flexible material, for example a living hinge of plastic, or through alternative hinge means. The cap 90A can also have a narrowed-width, extended lip 92 that can act as a grip to flip open the cap. The sealing head 60A can have a corresponding recess 93 on the exterior surface with similar width to the lip 92. When the cap 90A is in a closed position and covers the sealing head 60A, the extended lip is secured within the recess 93. The recess 93 has a depth corresponding to the thickness of the lip 92 so that when the cap 90A is in a closed state, the outer surface of the lip 92 is substantially flush with the remainder of the sealing head 60A. The recess 93 and lip 92 can also be releasably secured to each other with a connection mechanism (not shown), for example a male protrusion and female receptacle.

Figure 6A:
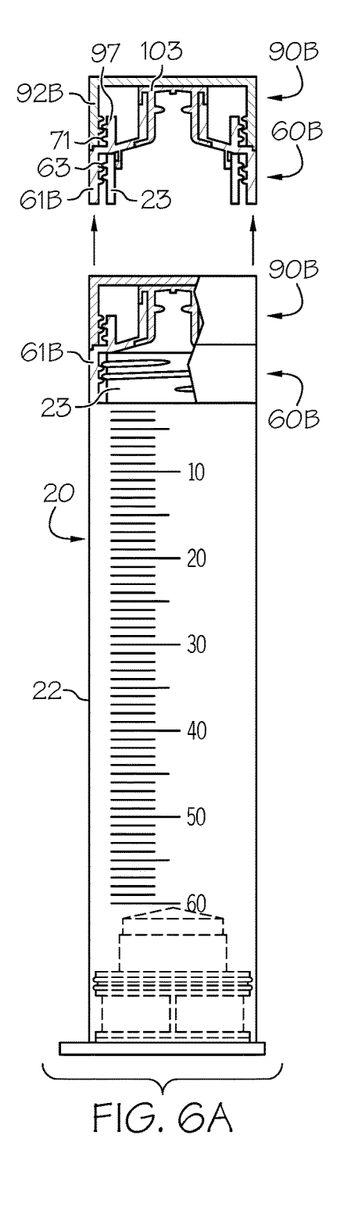
FIG. 6A is a partial cross-sectional side view of a second alternative example embodiment of the container shown in FIGS. 1A and 3A and an exploded cross sectional view of the cap and seal arrangement.
Figure 6B:
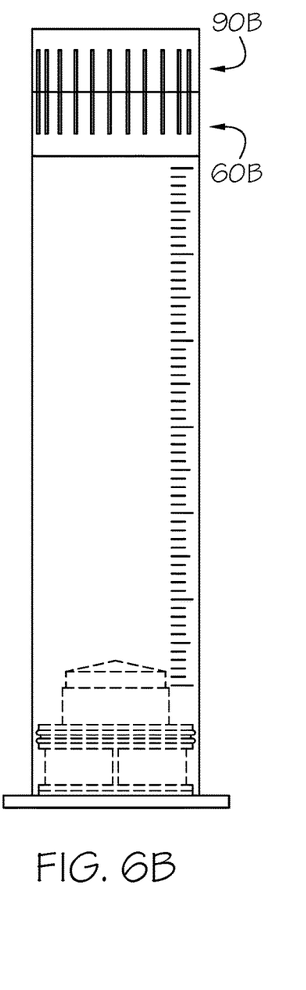
FIG. 6B is a side view of the example container shown in FIG. 6A.

A second example is shown in FIGS. 6A and 6B. Similar to the example in FIGS. 5A-C, the sleeve 22 includes the narrowed-diameter ring 23 with threading on the outer surface. And, an example sealing head 60B has a first circumferential wall 61B with threading 63 on the inner surface. The diameter of the first circumferential wall 61B is substantially equivalent to the diameter of the sleeve 22. And, the threading on the barrel ring 23 corresponds with the threading on the sealing head 60B. The sealing head 60B further includes a silicon seal 103 that extends from an external region of the sealing head and along the internal walls. The sealing head 60B also includes a second circumferential wall 97 having a smaller diameter than the first circumferential wall 61B. This second circumferential wall 97 includes a threaded outer surface 71. The example cap 90B has a shape and diameter similar to the cap 90A in FIGS. 5A-C. The cap 90B also has a threaded inner surface 92B that corresponds with the threaded inner surface 71 of the second circumferential wall 97. The cap 90B can be secured and removed with respect to the sealing head 60B by rotatably engaging and disengaging the corresponding threaded surfaces 92B, 71. As depicted in FIG. 6B, the cap 90B and the sealing head 60B can have grip features, for example ridges, around the outer circumference.

Figure 7A:
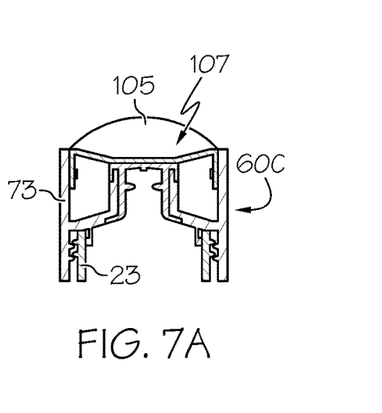
FIG. 7A is an isolated cross-sectional view of a third example embodiment of a cap and seal arrangement according to another example embodiment of the invention.
Figure 7B:
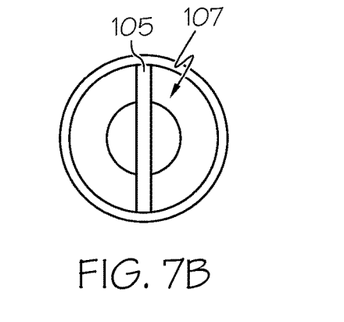
FIG. 7B is an isolated top view of the cap shown in FIG. 7A.

FIGS. 7A-7B show another example embodiment that can be secured with respect to the reduced-diameter barrel ring 23 on the sleeve 22. This example sealing head 60C has a threaded inner surface that corresponds with the threaded surface of the barrel ring 23. This seal 60C also has a vertically-extending outer circumference wall 73, which has a height that extends beyond the embodiments in FIGS. 5A-6B. A circular lid 107 that has a vertically-oriented circumferential wall is secured within the circumference of the wall 73 of the seal 60C. The lid 107 can be secured to the seal 60C through any fixation element, for example a pin, friction or adhesive. The lid 107 also has a fin or handle 105 extending diametrically across the lid. In order to either secure or detach the seal 60C from the ring 23, a user can then rotate the seal with respect to the ring barrel thread by applying rotational force to the lid handle using the fin 105 as a gripping surface.

Figure 8A:
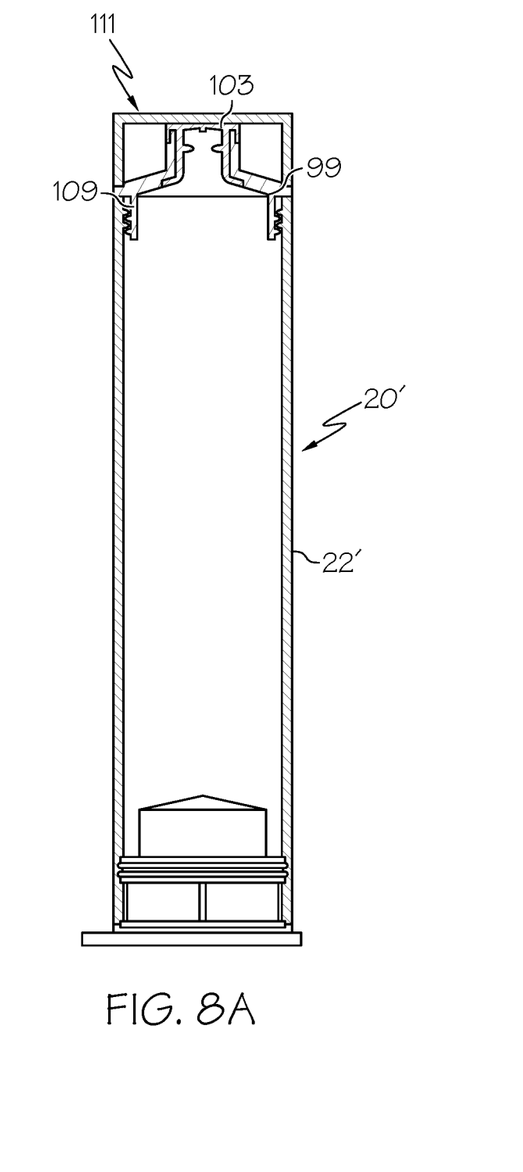
FIG. 8A is a partial cross-sectional side view of another example embodiment of a container according to the present invention.
Figure 8B:
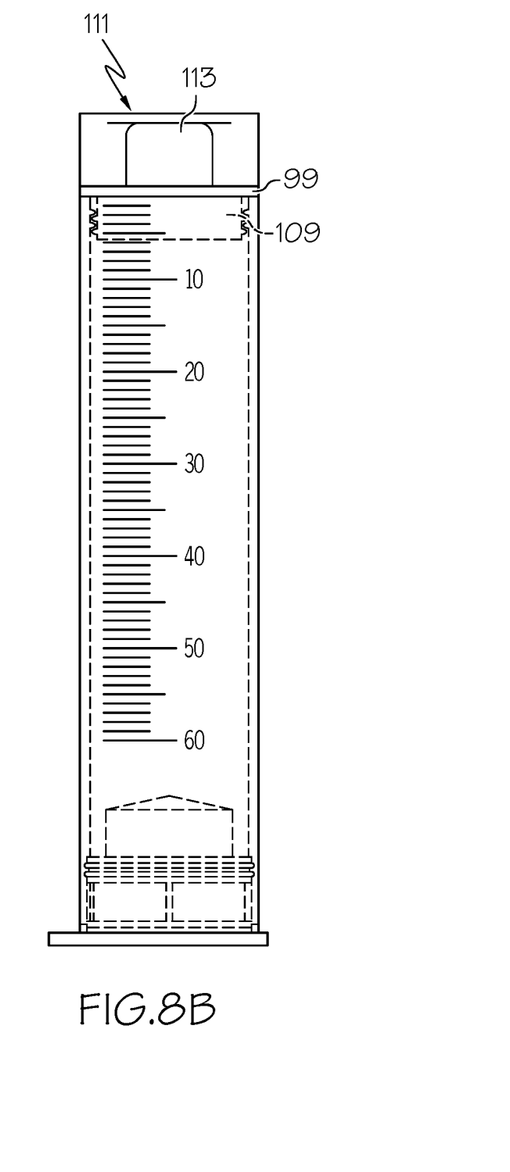
FIG. 8B is a side view of the container shown in FIG. 8A.
Figure 9A:
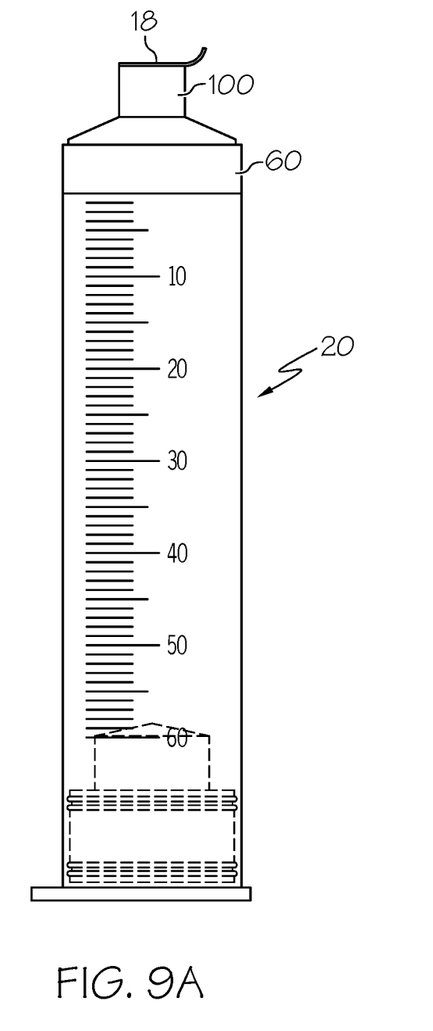
FIG. 9A is an isolated side view of another example embodiment of the container and the cap and seal arrangement.
Figure 9B:
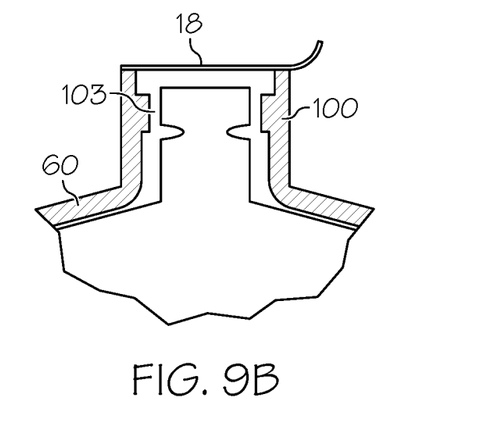
FIG. 9B is a detailed cross-sectional view of the cap and seal arrangement of FIG. 9A.
Figure 9C:
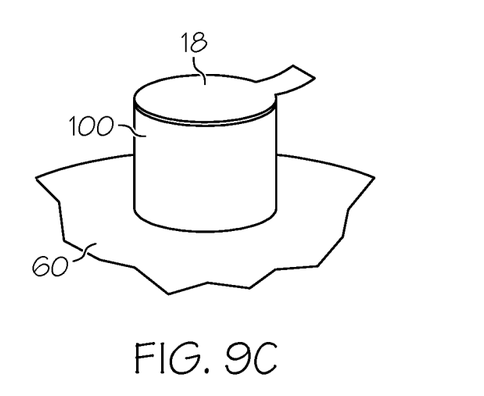
FIG. 9C is an enlarged and isolated perspective view of the cap and seal arrangement shown in FIG. 9A.
Figure 10:
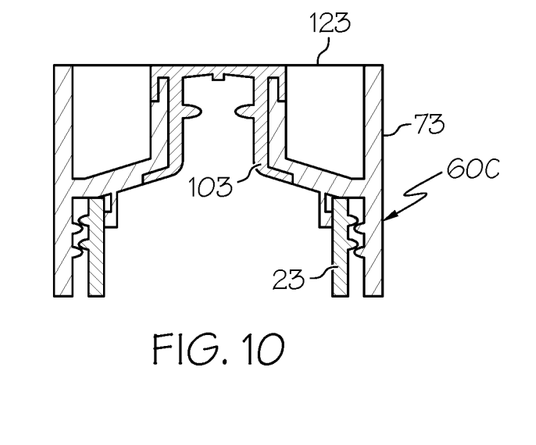
FIG. 10 is an isolated cross-sectional view of an alternative example embodiment of the seal and cap arrangement.

Still another example embodiment is shown in FIGS. 8A and 8B. The example sealing head 99 includes a circumferential wall 109 with male threading on the external face that secures within a female threaded sleeve 22' of barrel 20'. The wall 109 can alternatively be secured within the sleeve 22' through friction fit, snap-fitting, adhesive or other connection means. As depicted, a cap 111 can be placed over, and optionally secured to, the seal 99. The cap 111 can secure to the seal 99 or to the sealing head 99 by a snap-fitting, friction, threads or any suitable removable attachment method. As shown, the outer circumference of the cap 111 has a substantially identical diameter to the diameter of the sleeve 22'. As shown, the cap 11 can optionally have an indentation 113 for gripping and removal. FIGS. 9A-9C and FIG. 10 show alternative embodiments wherein a foil seal 18, 123 can be removably secured across the open top of the circumferential sealing head, for example with a removable adhesive, for prevention of contamination.

Figure 12:
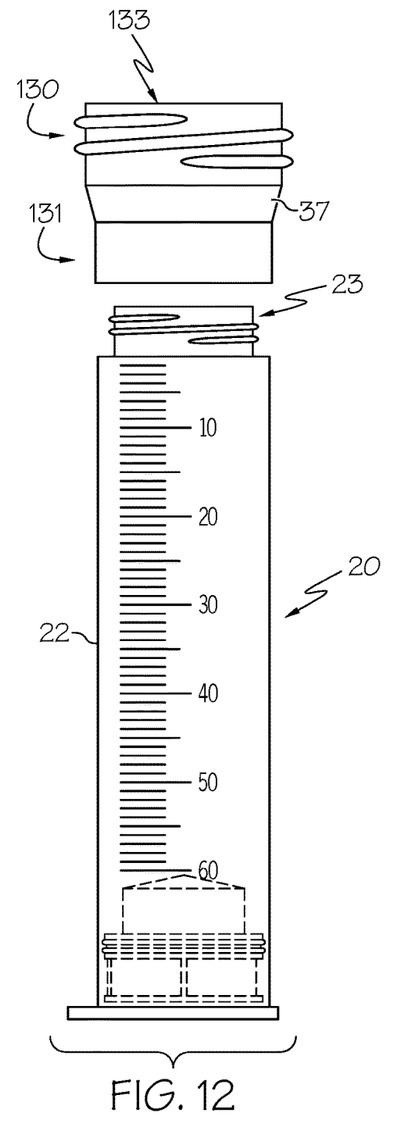
FIG. 12 is a side assembly view of the container of FIG. 5A and an adaptor.
Figure 13:
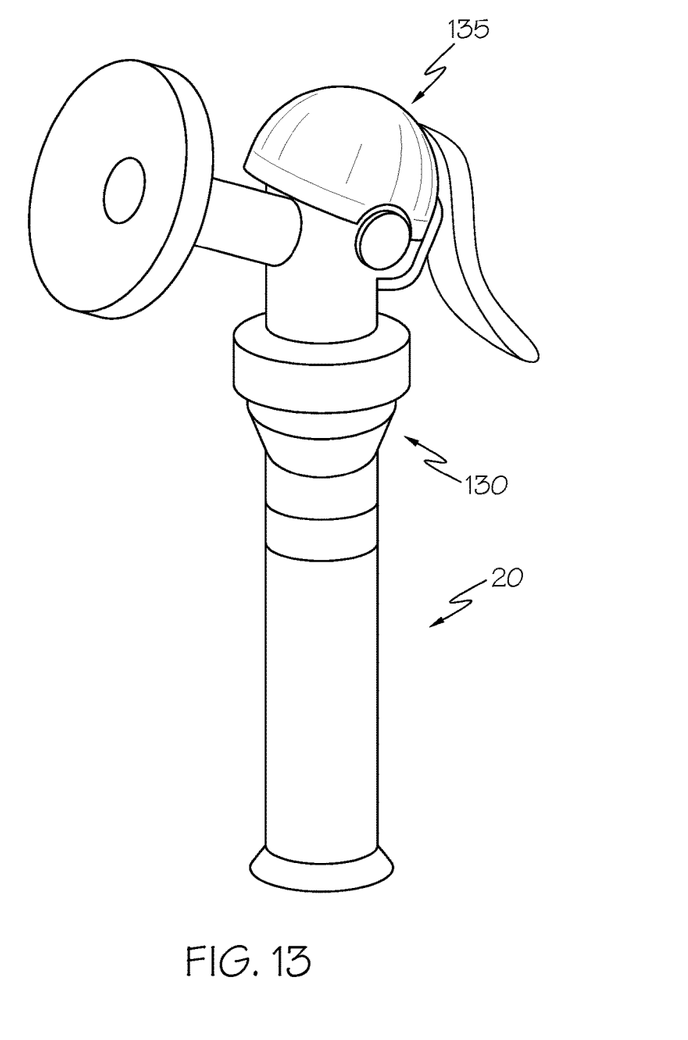
FIG. 13 is a perspective view of the container and adaptor of FIG. 12 in use in connection with a breast pump.

FIG. 12 shows an alternative use of the container 10 wherein an adapter 130 having a narrow-diameter lower portion 131 and a wider-diameter upper portion 133 can be secured to the barrel ring 23. For example, the lower portion 131 can have a circumferential outer diameter that is substantially equivalent to that of the sleeve 22 and a circumferential inner surface with threading that corresponds with the threading on the barrel ring 23. Additionally, the wider upper portion 133 can have a threaded circumferential outer surface. A transitional surface 37 connects the narrow lower portion 131 to the wider upper portion 133. As further shown in FIG. 13, the adaptor 130 can be secured to the container 20 for use with a commercially-available breast pump 135. The breast pump 135 can have a threaded inner circumference (not shown) that corresponds with the threaded outer circumference of the adaptor upper portion 133.

The material of construction of the container, according to example forms of the invention, can be chosen for compatibility of the containment system suitable for contact/storage/dispensing/mixing of enteral feeding and/or medication components that may be liquid, solid (powdered nutritional supplements or formula), suspensions (some medications etc), for example using food-grade plastics, composites, or the like. Moreover, the variable volume containment enabled by advancement and retraction of the syringe plunger within the containment barrel can be advantageous where freezing may cause a volume increase of the components stored therein, to maintain aseptic containment as the volume of contents increases or decreases. Furthermore, it is believed that the variable volume can allow for pressure changes to be neutralized resulting from any volume change (as by temperature changes or freezing) and may provide an indicator of boiling with a rapid increase in volume. The variable volume aspect of the invention also helps to maintain proper seal integrity in the face of internal pressure changes.

While the invention has been described with reference to preferred and example embodiments, it will be understood by those skilled in the art that a variety of modifications, additions and deletions are within the scope of the invention, as defined by the following claims.

What is claimed is:

1. A method of dispensing an enteral fluid, the method comprising:
    storing the enteral fluid in a container, the container comprising a barrel, a plunger translationally mounted in the barrel, and a sealing head for removable attachment to a proximal end of the barrel, the sealing head comprising a resealable port, and the sealing head and the barrel having substantially similar outer diameters;
    mounting the container in a dispensing pump; and
    operating the dispensing pump to deliver the enteral fluid through the resealable port.

2. The method of claim 1, wherein the substantially similar outer diameters of the sealing head and the barrel allow the container to lie flat in engagement within a receiver of the dispensing pump.

3. The method of claim 1, further comprising filling the container with the enteral fluid by moving the plunger away from the proximal end of the barrel, thereby increasing a contained volume defined within the container.

4. The method of claim 3, further comprising attaching a breast pump to the barrel via a coupling.

5. The method of claim 1, wherein the plunger comprises a plunger head in sealing contact with the barrel, the method further comprising attaching a plunger handle to the plunger head.

* * * * *